(12) United States Patent
Rogerson

(10) Patent No.: US 11,029,051 B2
(45) Date of Patent: Jun. 8, 2021

(54) SINGLE MODULE OPTIMIZING CONTROLLER CAPABLE OF OPERATING ONE OF A PLURALITY OF DIFFERENT TYPES OF HVACR SYSTEMS

(71) Applicant: AERIS ENVIRONMENTAL LTD, Rosebery (AU)

(72) Inventor: Christopher James Rogerson, Cleveland (AU)

(73) Assignee: AERIS ENVIRONMENTAL LTD

( * ) Notice: Subject to any disclaimer, the term of this patent is extended or adjusted under 35 U.S.C. 154(b) by 87 days.

(21) Appl. No.: 16/309,685

(22) PCT Filed: Jun. 15, 2017

(86) PCT No.: PCT/AU2017/050600
§ 371 (c)(1),
(2) Date: Dec. 13, 2018

(87) PCT Pub. No.: WO2017/214676
PCT Pub. Date: Dec. 21, 2017

(65) Prior Publication Data
US 2019/0331357 A1    Oct. 31, 2019

(30) Foreign Application Priority Data

Jun. 15, 2016  (AU) ................................ 2016902326
Oct. 24, 2016  (AU) ................................ 2016904319

(51) Int. Cl.
*F24F 11/46*    (2018.01)
*F24F 11/83*    (2018.01)
(Continued)

(52) U.S. Cl.
CPC ............. *F24F 11/46* (2018.01); *A61L 2/18* (2013.01); *B08B 9/023* (2013.01); *C09D 5/14* (2013.01);
(Continued)

(58) Field of Classification Search
CPC . F24F 11/46; F24F 11/83; F24F 11/89; G05B 13/021; C11D 3/38618; C11D 3/48
See application file for complete search history.

(56) References Cited

U.S. PATENT DOCUMENTS

2002/0162800 A1    11/2002  Back et al.
2006/0234621 A1*   10/2006  Desrochers ............. F24F 3/044
                                                        454/239
(Continued)

FOREIGN PATENT DOCUMENTS

CA    2791973    4/2013
CN    1359462    7/2002
(Continued)

OTHER PUBLICATIONS

European Search Report for EP Application No. 17812318.8 dated Dec. 10, 2019.
(Continued)

*Primary Examiner* — Vincent H Tran
(74) *Attorney, Agent, or Firm* — The Belles Group, P.C.

(57) ABSTRACT

Described herein is a single unit optimizing controller (100) capable of operating any known type of heating, ventilation, air conditioning and refrigeration HVACR system (an HVACR system is denote by reference numeral (101)), which include all ACR systems. HVACR system (101) takes the form of an air conditioning unit. The controller includes a communications section (102) for communicating with one or more remote controller terminal in the form of a web application (103) and a control section (104). The air conditioning unit of HVACR system (101) includes at least one cooling unit having a compressor wherein the control section is operatively associated with HVACR system (101) for selectively activating or deactivating the at least one cooling
(Continued)

unit based on one or more settings received from web application (103) via communications section (102).

10 Claims, 5 Drawing Sheets

(51) Int. Cl.
| | | |
|---|---|---|
| F24F 11/89 | (2018.01) | |
| F24F 11/56 | (2018.01) | |
| A61L 2/18 | (2006.01) | |
| B08B 9/023 | (2006.01) | |
| C09D 5/14 | (2006.01) | |
| C09D 139/06 | (2006.01) | |
| C11D 1/22 | (2006.01) | |
| C11D 3/20 | (2006.01) | |
| C11D 3/386 | (2006.01) | |
| C11D 3/48 | (2006.01) | |
| C11D 11/00 | (2006.01) | |
| F25D 17/00 | (2006.01) | |
| F25D 31/00 | (2006.01) | |
| G05B 13/02 | (2006.01) | |
| F24F 110/10 | (2018.01) | |
| B08B 3/08 | (2006.01) | |
| C08K 5/19 | (2006.01) | |
| F28D 21/00 | (2006.01) | |
| F28G 9/00 | (2006.01) | |

(52) U.S. Cl.
CPC .............. *C09D 139/06* (2013.01); *C11D 1/22* (2013.01); *C11D 3/2068* (2013.01); *C11D 3/38618* (2013.01); *C11D 3/48* (2013.01); *C11D 11/0041* (2013.01); *F24F 11/56* (2018.01); *F24F 11/83* (2018.01); *F24F 11/89* (2018.01); *F25D 17/005* (2013.01); *F25D 31/005* (2013.01); *G05B 13/021* (2013.01); *A61L 2202/17* (2013.01); *B08B 3/08* (2013.01); *C08K 5/19* (2013.01); *F24F 2110/10* (2018.01); *F24F 2221/22* (2013.01); *F25B 2700/19* (2013.01); *F25B 2700/21* (2013.01); *F28D 2021/0068* (2013.01); *F28F 2265/20* (2013.01); *F28G 9/00* (2013.01)

(56) References Cited

U.S. PATENT DOCUMENTS

| | | |
|---|---|---|
| 2007/0004596 A1 | 1/2007 | Kritzler |
| 2009/0252701 A9* | 10/2009 | Kritzler ............... C08K 5/0058 424/78.31 |
| 2009/0283113 A1 | 11/2009 | Münch |
| 2014/0149270 A1 | 5/2014 | Lombard et al. |
| 2015/0192374 A1* | 7/2015 | McNeice ................. F24F 1/14 62/467 |
| 2015/0291993 A1* | 10/2015 | Vela ....................... C12Q 1/06 210/745 |
| 2016/0061468 A1 | 3/2016 | Alexander et al. |
| 2016/0146495 A1 | 5/2016 | Malve et al. |
| 2016/0156299 A1 | 6/2016 | Romanowich et al. |
| 2016/0273856 A1* | 9/2016 | Seippel .................. F28G 15/00 |
| 2016/0327323 A1* | 11/2016 | Goel .................... F25B 39/028 |
| 2017/0234566 A1* | 8/2017 | Gerszewski .......... G06F 21/604 700/276 |
| 2017/0299209 A1* | 10/2017 | Bushmeyer ............ G05B 15/02 |
| 2017/0314804 A1* | 11/2017 | Kannan ............... H04L 12/2825 |
| 2017/0356669 A1* | 12/2017 | Gonia ..................... F24F 11/30 |
| 2017/0357490 A1* | 12/2017 | Park ....................... G05B 15/02 |

FOREIGN PATENT DOCUMENTS

| | | |
|---|---|---|
| CN | 100389655 | 7/2006 |
| EP | 0274831 | 7/1988 |
| EP | 0274831 A2 | 7/1988 |
| EP | 1946638 A2 | 7/2008 |
| WO | 0106248 | 1/2001 |
| WO | WO 2004/103071 | 12/2004 |
| WO | 2005037585 A1 | 4/2005 |
| WO | 2005041659 A1 | 5/2005 |
| WO | 2015183678 A1 | 12/2015 |
| WO | 2016032862 A1 | 3/2016 |

OTHER PUBLICATIONS

International Search Report for corresponding Applicaton No. PCT/AU2017/050600, dated Sep. 7, 2017. WO.

Chinese Office Action issued in Chinese Application No. 201780050281.3 dated Jul. 3, 2020.

* cited by examiner

SINGLE MODULE OPTIMIZING CONTROLLER CAPABLE OF OPERATING ONE OF A PLURALITY OF DIFFERENT TYPES OF HVACR SYSTEMS

CROSS-REFERENCE TO RELATED PATENT APPLICATIONS

The present application is a U.S. national stage application under 35 U.S.C. § 371 of PCT Application No. PCT/AU2017/050600, filed Jun. 15, 2017, which claims priority to Australian Patent Application No. 2016902326, filed Jun. 15, 2016; and Australian Patent Application No. 2016904319, filed Oct. 24, 2016. The disclosures of the aforementioned priority applications are incorporated herein by reference in their entireties.

FIELD OF THE INVENTION

The present invention relates to controllers and controller optimization for Heating, Ventilation, Air Conditioning and Refrigeration ("HVACR") systems. While some embodiments will be described herein with particular reference to HVACR controllers, it will be appreciated that the invention is not limited to such a field of use, and is applicable in other contexts, for example, the controlling of functionality in refrigeration or cool room systems and the gathering and exporting of data from third party HVACR and non-HVACR systems.

BACKGROUND

Any discussion of the background art throughout this specification should in no way be considered as an admission that such art is widely known or forms part of common general knowledge in the field.

Broadly, HVACR systems have as their goal the provision of comfort in a space (for example in an office building, a factory, a vehicle, a shopping center, cool rooms and freezer rooms, refrigerated shipping containers or refrigerated vehicles).

Climate control and more specifically air conditioning has now become a virtual necessity within most indoor environments and especially in commercial and industrial settings. The use of air conditioning to maintain a conformable temperature in a working environment can often increase productivity within that environment. As such, the manufacturing and implementation of heating, ventilation and air conditioning (HVAC) systems is a well established industry.

Air Conditioning systems come in two primary forms DX (Direct Expansion of a refrigerant) or chilled water systems.

DX Systems DX Air conditioning or refrigeration units catering for large spaces comprise a circuit such as shown the circuit referenced by numeral 400 in FIG. 4. Circuit 400 comprises a compressor 4 which pumps a refrigerant gas to a high pressure and temperature. From compressor 4 the refrigerant enters a heat exchanger 1 (called a condensing coil or condenser) where it loses heat energy to the outside, cools and condenses into its liquid phase. An expansion valve 2 regulates the refrigerant gas to flow at a proper rate and causes it to cool by expansion to a lower pressure. The liquid refrigerant is returned to another heat exchanger 3 (called an evaporation coil or evaporator where the refrigerant absorbs energy (heat) from the air and then returns the refrigerant to the compressor for the cycle to be repeated. Not shown in FIG. 4 are various air circulation systems which draw air from the space being air conditioned or refrigerated and blow that air over heat exchanger 3, or systems which draw air from an outdoor area and blow that air over exchanger 1. These air flow parts of the system require fan(s) to produce circulation over heat exchange surfaces and through one or more dust filters to maintain air quality.

Chilled water systems are also well-known in the art. These systems include many parts, with the primary machines being the chiller, which can comprise of different types of compressors for different types of building loads and applications.

Known compressors include:
Chillers with Reciprocating Compressors.
Chillers with Scroll Compressors.
Chillers with Screw Compressors (with or without variable speed drive).
Centrifugal Compressors (with or without variable Speed drive).
Chillers with TurboCore compressors.

The chiller is in essence a very large DX system, but instead of producing a cold refrigerant to reticulate to an evaporator system it produces chilled water generally in the range of 5° C. to 9° C. via a pumping system to a coil in a fan assisted chamber connected to air duct work reticulated throughout an area. This water then returns to the chiller(s) to be re-cooled. As per DX systems, the refrigerant within the chiller vessel needs to be cooled. This is done by passing the refrigerant from the chiller through a similar air-cooled condenser or by passing water over the warm refrigerant tubes within the chiller and this water is cooled by running it through an evaporative water cooling tower.

Presently, an air conditioning unit (DX or chilled water) requires a controller to control the functioning of the system. Controllers respond to a temperature sensor within the relevant air space to simply turn an air conditioner on or off if it is a fixed speed system, or varying the speed of the compressor if it is variable speed. This, in turn, changes the capacity of the compressor relative to the internal temperature load requirements and depending on the temperature of the space to be cooled, in comparison to a preset temperature.

Such controllers are made to control a specific brand and model of cooling device and, as such, are each limited to use with that particular device. These controllers are manually set to a predetermined temperature, that is, a desired temperature is selected and the controller is then left to control the air conditioning unit. Such known controllers only regulate basic control functions and manufacturers apply almost identical functionality to allow the system to achieve a preset desired temperature. The ultimate aim of these controllers is to maintain a room or certain space at a selected temperature. For example, if this temperature is 22° C. the controller will turn the compressor on when the room is 22.5° C. and turn the compressor off at 21.5° C. providing an average of 22° C. or vary the speed of the compressor so the system operates within a similar operating band.

As such the firmware, hardware and software in HAVC system controllers is very simple in terms of their functionality and very limited in terms of compatibility from one system to another.

More recently, there has been an interest in energy savings, due to both awareness of environmental benefits and cost savings. This has been considered in part by HVAC controller developers. However, the notion of compressor optimisation has not previously been widely investigated and developed. In the few cases where it has been considered, the existing optimising functionality only measured the electric power consumption of the compressor and attempted to optimize energy efficiency for example by changing the duration of on and off periods of compressor operation. The majority of these systems only reduce average energy usage of the compressor (kWh) only and have no effect on Peak Demand. A vast majority of individual Air Conditioning and Refrigeration (ACR) systems and indeed non ACR systems and components today have communication ports which allow systems such as a Building Management System, BMS to interface to the system or its components and collect information about the system or parts of it and even change parameters within the system or parts. However, in respect of ACR systems, the purpose of these control systems is to make the systems operate to a required temperature set point and within a temperature operating range rather than to optimize the energy consumption of the system as a whole.

These controllers come in many different forms, such as:
  Electro Mechanical.
  Electronic, such as:
    Stand Alone.
    Networked.
    Integrated.
    Internet of Things (IoT).
    Web-based.
  Programmable Logic Control (PLC).
  Building Management System (BMS).

There is a mind-set in the HVAC and refrigeration controller industry that the power savings brought about by present controllers are difficult or even impossible to improve upon in relation to their power-saving efficiency. There is a perception that it is at an acceptable level that cannot be improved, or at least is not worth improving given the perception that any power savings achieved will be relatively minimal and not worth the research and development costs.

The present inventors have found that it is possible to obtain surprising improvements in energy efficacy and to reduce electricity consumption significantly without loss of air conditioned comfort by use of a controller which not only switches the compressor on and off but which also simultaneously controls one or more of the following variables: rate of refrigerant circulation, water flow through the chillers, air flow rate (fan speed) across the condenser coils, airflow rate across the evaporator coils, refrigerant temperature, refrigerant pressure, pressure drop across filters, and the like, as well as the turn on and turn off temperature at which the compressor is actuated or deactivated.

The inventors also found that one specific challenge faced when seeking to optimise the energy efficiency of water based cooling or chiller systems is the constantly changing biological load in the cooling water and biofilm formation on equipment surfaces.

Air conditioning and refrigeration cooling coils exhibit surfaces which are constantly wet due to the condensation of water from the air being cooled and forced through the coil. All surfaces which are continuously wet grow biofilm. Biofilm is the colonisation of a substrate by various bacteria and fungi which multiply on the substrate surface in a symbiotic colony where nutrients are shared by the various organisms.

Biofilms are seriously deleterious to the long term effective, efficient operation of a cooling coil for three main reasons:

Firstly, biofilms are excellent insulators between the heat exchange surface and the air being cooled and therefore seriously decrease the heat exchange efficiency of a coil. This decrease in efficiency grows as the biofilm grows thicker.

Secondly, as for all living organisms, the cells in the biofilm exude waste products which are acidic and these cause progressive corrosion of the unanodised aluminium heat exchange surfaces.

Thirdly, as the gap between adjacent cooling fins decreases with the growth of biofilm less air passes through the coil at the set speed of the fan or else in the case of variable speed fans, the fans must work much harder and therefore consume significantly more power to achieve the required set point temperature.

These three factors all present a significant challenge to the increased energy efficiency of the cooling device.

SUMMARY OF THE INVENTION

In accordance with a first aspect of the present invention there is provided a single module optimizing controller capable of operating any one of a plurality of different types of heating, ventilation, air conditioning and refrigeration (HVACR) system, said system including at least one cooling unit, the controller including:
  a communications section for communicating with or one or more remote controller terminal; and
  a control section operatively associated with the one HVACR system for selectively activating or deactivating the at least one cooling unit based on one or more settings received from the remote controller terminal via the communications section.

In one embodiment, the HVACR system includes chilled water system having water circulation through a cooling coil and a fan for directing air across the cooling coil, wherein the control section selectively controls one or more of: the water circulation flow rate through the coil; and the fan speed controlling designated air flow through the coil.

In an embodiment, the HVACR system includes at least one sensor for sensing an output of the HVACR system, the controller responsive to the at least one sensor such that the selectively activating or deactivating the at least one cooling unit is influenced by the at least one sensor. In an embodiment, the at least one sensor is connected to the control section. In an embodiment, the at least one sensor includes a current transformer for measuring system current and for control, measurement, and system functionality, and operation and alarming purposes. In an embodiment, the at least one sensor includes a temperature sensor for measuring system space or environment temperature. In an embodiment, the at least one sensor includes a pressure sensor for measuring the pressure drop across a filter of the HVACR system and/or the cooling coil. In an embodiment, the at least one sensor includes a flow sensor for measuring a water flow rate through the chilled water system. In an embodiment, the at least one sensor includes a humidity sensor for measuring the air humidity.

In another embodiment, the HVACR system includes a plurality of sensors each for sensing a unique output of, or input to, the HVACR system, the controller responsive to the sensors such that the selectively activating or deactivating the at least one cooling unit is influenced by one or more of the plurality of sensors. In an embodiment, the plurality of sensors includes a temperature sensor. In an embodiment, the plurality of sensors includes a pressure sensor. In an embodiment, the plurality of sensors includes a flow sensor. In an embodiment, the plurality of sensors includes a biofilm growth sensor for sensing biofilm growth in a water cooling tower and/or a water circuit of the HVACR system.

In an embodiment, the communications section includes at least one communications port for enabling external connection to the one or more remote controller terminal. In an embodiment, the remote user terminal is a computer capable of running control software configurable to operate the any one of a plurality of different types of HVACR systems to enable the desired functioning of the controller and systems. In an embodiment, the control software includes a web application. In an embodiment, the web application includes an end user interface. In an embodiment, the web application includes a technician interface. In an embodiment, the communications section includes a storage database for receiving and storing operational data from the controller. In an embodiment, the operational data is accessible through the web application.

In another embodiment, the control section includes at least one I/O points. In a further embodiment, the control section includes up to 8 I/O points. In a yet further embodiment, the control section includes up to 32 universal I/O points.

In an embodiment, the different types of HVACR systems include one or more of the group including: a single compressor; a multiple compressor; a chiller for an air conditioning system; a chiller for a refrigeration system; an inverter system, and a variable refrigerant flow (VRF) system.

In an embodiment, the controller has a footprint of approximately 120 mm by 120 mm. In an embodiment, the controller has a footprint of approximately 100 mm by 100 mm. In an embodiment, the controller has a footprint of approximately 80 mm by 80 mm.

In an embodiment, the HVACR system includes a plurality of cooling units and the controller is able to simultaneously control each of these cooling units.

In an embodiment, at least one of the plurality of cooling units is a different type of unit to at least one other of the cooling units.

In accordance with a second aspect of the present invention there is provided an HVACR system including:
    an optimizing controller according to the first aspect; and
    at least one cooling unit operatively associated with the controller.

In one embodiment, the at least one cooling unit takes the form of a chilled water system having water circulation through a cooling coil and a fan for directing air across the cooling coil, wherein the control section selectively controls one or more of: the water circulation flow rate through the coil; and the fan speed controlling designated air flow through the coil.

In an embodiment, the HVACR system includes at least one sensor for sensing an output of the HVACR system, the controller responsive to the at least one sensor such that the selectively activating or deactivating the at least one cooling unit is influenced by the at least one sensor. In an embodiment, the at least one sensor is connected to the control section. In an embodiment, the at least one sensor includes a current transformer for measuring system current and for control, measurement, and system functionality, and operation and alarming purposes. In an embodiment, the at least one sensor includes a temperature sensor for measuring system space or environment temperature. In an embodiment, the at least one sensor includes a pressure sensor for measuring the pressure drop across a filter of the HVACR system and/or the cooling coil. In an embodiment, the at least one sensor includes a flow sensor for measuring a water flow rate through the chilled water system. In an embodiment, the at least one sensor includes a humidity sensor for measuring the air humidity.

In another embodiment, the HVACR system includes a plurality of sensors each for sensing a unique output of, or input to, the HVACR system, the controller responsive to the sensors such that the selectively activating or deactivating the at least one cooling unit is influenced by one or more of the plurality of sensors. In an embodiment, the plurality of sensors includes a temperature sensor. In an embodiment, the plurality of sensors includes a pressure sensor. In an embodiment, the plurality of sensors includes a flow sensor. In an embodiment, the plurality of sensors includes a biofilm growth sensor for sensing biofilm growth in a water cooling tower and/or a water circuit of the at least one cooling unit.

In an embodiment, the communications section includes at least one communications port for enabling external connection to the one or more remote controller terminal. In an embodiment, the remote user terminal is a computer capable of running control software configurable to operate the any one of a plurality of different types of HVACR systems to enable the desired functioning of the controller and systems. In an embodiment, the control software includes a web application. In an embodiment, the web application includes an end user interface. In an embodiment, the web application includes a technician interface. In an embodiment, the communications section includes a storage database for receiving and storing operational data from the controller. In an embodiment, the operational data is accessible through the web application.

In another embodiment, the control section includes at least one I/O points. In a further embodiment, the control section includes up to 8 I/O points. In a yet further embodiment, the control section includes up to 32 universal I/O points.

In an embodiment, the different types of HVACR systems include one or more of the group including: a single compressor; a multiple compressor; a chiller for an air conditioning system; a chiller for a refrigeration system; an inverter system, and a variable refrigerant flow (VRF) system.

In an embodiment, the controller has a footprint of approximately 120 mm by 120 mm. In an embodiment, the controller has a footprint of approximately 100 mm by 100 mm. In an embodiment, the controller has a footprint of approximately 80 mm by 80 mm.

In an embodiment, the HVACR system includes a plurality of cooling units and the controller is able to simultaneously control each of these cooling units.

In an embodiment, at least one of the plurality of cooling units is a different type of unit to at least one other of the cooling units.

In accordance with a third aspect of the present invention there is provided a method for controlling an HVACR system according to the second aspect including:
    providing external connection to a remote controller terminal;
    via the remote controller terminal, configuring the controller to optimally operate the at least one cooling unit.

In accordance with a fourth aspect of the present invention there is provided a method for reducing the energy usage of an HVACR system having at least one evaporator coil including:
    providing an optimizing controller according to the first aspect for controlling the functioning of the HVACR system; and providing a coil treatment to the at least one evaporator coil, such that the use of the controller in conjunction with the coil treatment reduces the energy usage of the HVACR system by over 15%.

In an embodiment, the use of the controller in conjunction with the coil treatment reduces the energy usage of the HVACR system by over 18%.

In an embodiment, the use of the controller in conjunction with the coil treatment reduces the energy usage of the HVACR system by over 20%.

In an embodiment, the coil treatment includes:
  i) a first enzymic cleaning step comprising contacting the coil with an enzymic cleaning solution to provide a cleaned coil; and
  ii) a second step comprising coating the cleaned coil with a biostatic polymeric coating.

In an embodiment, the enzymic cleaning solution comprises one or more of a protease, amylase, cellulase or lipase. In another embodiment, the enzymic cleaning solution comprises a protease and a biostatically effective phenoxyalcohol. In yet another embodiment, the enzymic cleaning solution comprises a protease, a water soluble glycol ether solvent and at least one anionic hydrotrope such as an alkali metal alkylarylsulfonate. In yet another embodiment, the enzymic cleaning solution comprises one or more enzymes (for instance a protease and an amylase), a biocidal quaternary ammonium biocide, and an anionic hydrotrope.

In an embodiment, the biostatic film comprises a phenolic biocide and polyvinylpyrrolidone or polyvinylpyrrolidone polymers or copolymers, such as acrylic copolymer based compositions, methacrylic copolymer based compositions, vinyl copolymer based compositions, epoxy resins, epoxy esters, and mixtures thereof.

In an embodiment, the biostatic film comprises a polyvinylpyrrolidone/polyvinylacetate copolymer complexed with triclosan.

In an embodiment, the biostatic film comprises a quaternary ammonium biocide and a compatible polymer, such as polyvinyl alcohol, or a half ester of maleic anhydride/alkylvinylether copolymer complexed with a quaternary ammonium biocide.

In accordance with a fifth aspect of the present invention there is provided a system including:
  at least one HVACR system including at least one cooling unit; and
  an optimizing controller having:
    a communications section for communicating with one or more remote controller terminal; and
    a control section operatively associated with the one HVACR system for selectively activating or deactivating the at least one cooling unit based on one or more settings received from the remote controller terminal via the communications section.

In one embodiment, the at least one cooling unit takes the form of a chilled water system having water circulation through a cooling coil and a fan for directing air across the cooling coil, wherein the control section selectively controls one or more of: the water circulation flow rate through the coil; and the fan speed controlling designated air flow through the coil.

In an embodiment, the system includes at least one sensor for sensing an output of the at least one HVACR system, the controller responsive to the at least one sensor such that the selectively activating or deactivating the at least one cooling unit is influenced by the at least one sensor. In an embodiment, the at least one sensor is connected to the control section. In an embodiment, the at least one sensor includes a current transformer for measuring system current and for control, measurement, and system functionality, and operation and alarming purposes. In an embodiment, the at least one sensor includes a temperature sensor for measuring system space or environment temperature. In an embodiment, the at least one sensor includes a pressure sensor for measuring the pressure drop across a filter of the at least one HVACR system and/or the cooling coil. In an embodiment, the at least one sensor includes a flow sensor for measuring a water flow rate through the chilled water system. In an embodiment, the at least one sensor includes a humidity sensor for measuring the air humidity.

In another embodiment, the system includes a plurality of sensors each for sensing a unique output of, or input to, the at least one HVACR system, the controller responsive to the sensors such that the selectively activating or deactivating the at least one cooling unit is influenced by one or more of the plurality of sensors. In an embodiment, the plurality of sensors includes a temperature sensor. In an embodiment, the plurality of sensors includes a pressure sensor. In an embodiment, the plurality of sensors includes a flow sensor. In an embodiment, the plurality of sensors includes a biofilm growth sensor for sensing biofilm growth in a water cooling tower and/or a water circuit of the at least one cooling unit.

In an embodiment, the system includes one or more remote controller terminals and the communications section includes at least one communications port for enabling external connection to the one or more remote controller terminals. In an embodiment, the remote user terminal is a computer capable of running control software configurable to operate the any one of a plurality of different types of HVACR systems to enable the desired functioning of the controller and systems. In an embodiment, the control software includes a web application. In an embodiment, the web application includes an end user interface. In an embodiment, the web application includes a technician interface. In an embodiment, the communications section includes a storage database for receiving and storing operational data from the controller. In an embodiment, the operational data is accessible through the web application.

In another embodiment, the control section includes at least one I/O points. In a further embodiment, the control section includes up to 8 I/O points. In a yet further embodiment, the control section includes up to 32 universal I/O points.

In an embodiment, the different types of HVACR systems include one or more of the group including: a single compressor; a multiple compressor; a chiller for an air conditioning system; a chiller for a refrigeration system; an inverter system, and a variable refrigerant flow (VRF) system.

In an embodiment, the controller has a footprint of approximately 120 mm by 120 mm. In an embodiment, the controller has a footprint of approximately 100 mm by 100 mm. In an embodiment, the controller has a footprint of approximately 80 mm by 80 mm.

In an embodiment, the at least one HVACR system includes a plurality of cooling units and the controller is able to simultaneously control each of these cooling units.

In an embodiment, at least one of the plurality of cooling units is a different type of unit to at least one other of the cooling units.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Preferred embodiments of the disclosure will now be described, by way of example only, with reference to the accompanying drawings in which.

DETAILED DESCRIPTION

Figure 1A:
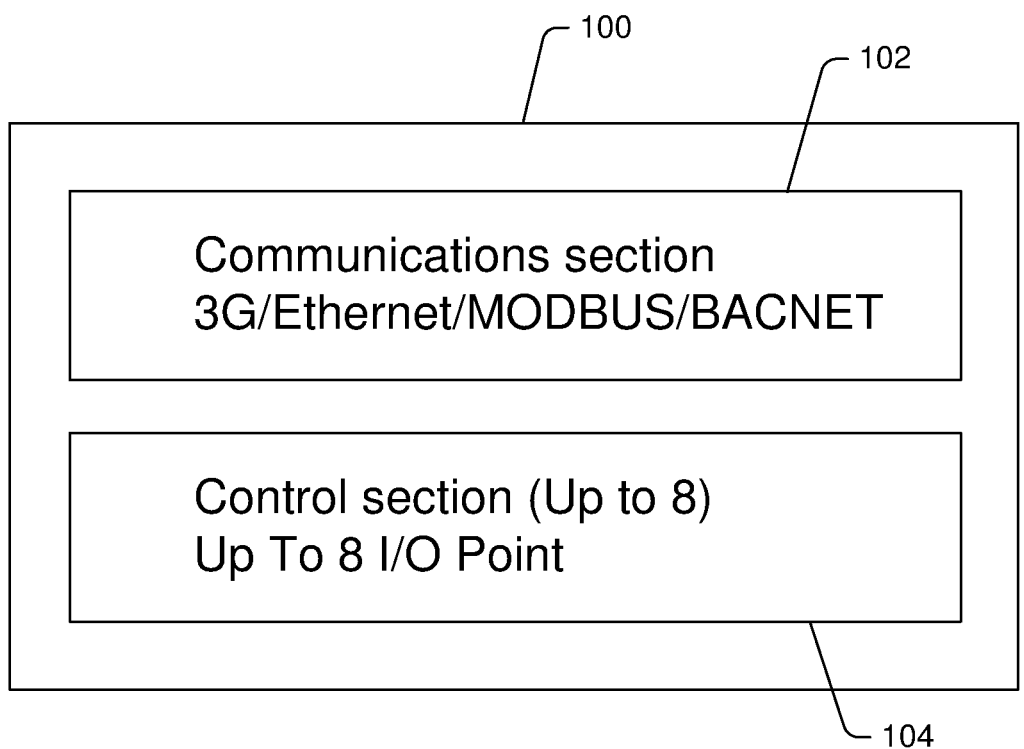
FIG. 1A is a conceptual block representation of a controller according to an embodiment of the invention.
Figure 2:
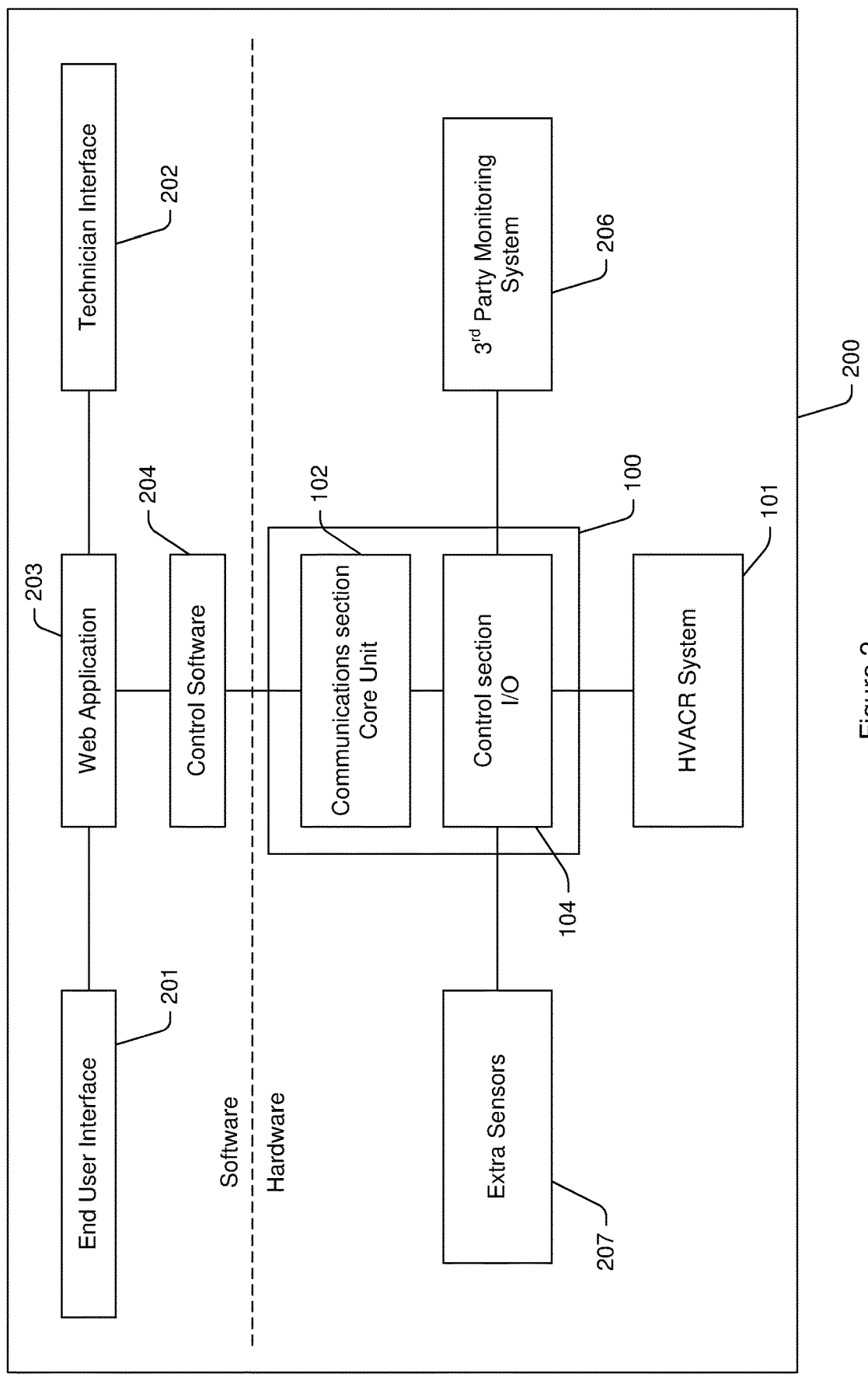
FIG. 2 is a block diagram of a system including the controller of FIG. 1A.

Referring initially to FIGS. 1A and 2, there is provided a single module optimizing controller 100 capable of operating any known type of heating, ventilation, air conditioning and refrigeration HVACR system (an HVACR system is denote by reference numeral 101), which include all ACR systems. In the preferred embodiments discussed herein, HVACR system 101 takes the form of an air conditioning unit. However, it will be appreciated that controller 100 can be used with virtually any HVACR system and with many other systems including refrigeration systems (this will be discussed in detail further below). The controller includes a communications section 102 for communicating with the internet, the cloud, a central server system and one or more remote controller terminal in the form of a web application 103, and a control, measuring, monitoring and optimisation section (referred to as control section 104). The air conditioning unit of HVACR system 101 includes at least one cooling unit having a compressor wherein the control section is operatively associated with HVACR system 101 for selectively activating or deactivating the at least one cooling unit based on one or more settings received from web application 103 via communications section 102.

Referring more particularly to FIG. 2, the block diagram of controller 100 within an entire end-to-end system 200 includes:

An end user interface 201 which includes the elements of the web application visible to an end user.

A technician Interface 202 which includes the elements of the web application visible to a technician.

A web application 203 in the form of a website served from communications section 102 with the ability to control various parameters.

Control, operation and interface software (referred to as control software 204) in the form of applications running on the communications section 102. The primary application will control the inputs/outputs of HVACR system 101 and log data. There will be supplementary applications for supervising the system, sending system messages, and other functionality.

Communications section 102 in the form of conventional Core Unit hardware with 3G/Network connectivity.

Control section 104 in the form of conventional I/O hardware with the required digital and analogue inputs and outputs.

HVACR System 101 representing one of many types of air conditioning or refrigeration systems.

A third party monitoring system 206 representing one of many types external systems with a RS232, RS485, Modbus or Demand Response Enabling Device (DRED) interface, for example in one embodiment third party monitoring system 206 includes a power meter, third party AC systems, and third party operating systems.

Extra Sensors 207 representing one of many types of extra sensors including but not limited to thermistors, current sensors (which include current transformers for measuring system current and are also used for control, measurement, and system functionality, and operation and alarming purposes), pressure sensors, and flow rate sensors, amongst others.

In some preferred embodiments, communications section 102 and control section 104 are combined into a single device, but are conceptually separated in this description based on their relative functions. Communications section 102 enables communications to and from controller 100 and is capable of being used for: receiving and relaying commands to controller 100; and receiving and storing data from controller 100. Communications section 102 includes an inbuilt 3G modem which is accessed via an allocated IP address for the controller which allows the stored data to be downloaded, deciphered and reported as required. Furthermore, communications section 102 allows the sending of alarms to a receiver and, in response to an alarm or as desired, the communications section further allows an authorized technician to adjust any settings within controller 100. Furthermore, communications section 102 includes wired and wireless communications capabilities.

The specific embodiment of the communications section 102 includes the following hardware:

A SIM card holder, allowing use of a 3G SIM card.

An SD card holder for expandable memory.

A processor running embedded software.

An Ethernet connection for a Local Area Network (LAN).

Antenna connections for a 3G signal.

Communications section 102 runs off 12V power supplied through a power connector and, furthermore, provides power and a USB connection to interface with control section 104. Communications section 102 provides driver firmware for control section 104. Also, communications section 102 provides standard modem/router features including:

Dynamic Host Configuration Protocol (DHCP).
Virtual Private Network (VPN).
Firewall.
Mandatory Access Control (MAC)/IP/Port Filtering.
Dynamic Domain Name System (DNS).
Network Time.
Event Logging.
System Watchdog.
Secure Shell (SSH).

However, it will be appreciated to those skilled in the art that in other embodiments, comparable alternative components are used as desired.

Control section 104 takes the form of I/O control devices known as 'Aeris Universal I/O'. Controller section 104 includes a single I/O layer with up to 32 I/O points.

The specific embodiment of the control section 104 includes the following hardware configuration possibilities:

Sixteen electrically isolated digital input/outputs.
One electrically isolated 4 to 20 mA analogue output. This requires external loop power.
One electrically isolated 0-10 VDC analogue output.
Eight 4 to 20 mA analogue inputs.
Three current transformer inputs.
Two two-wire PT100 thermistor inputs.
Four resistive temperature sensors.
A serial port that can be configured for RS232, RS422, RS485, or MODBUS port connectors.

The above inputs/outputs can be configured as universal points changing between digital and analogue.

Figure 1B:
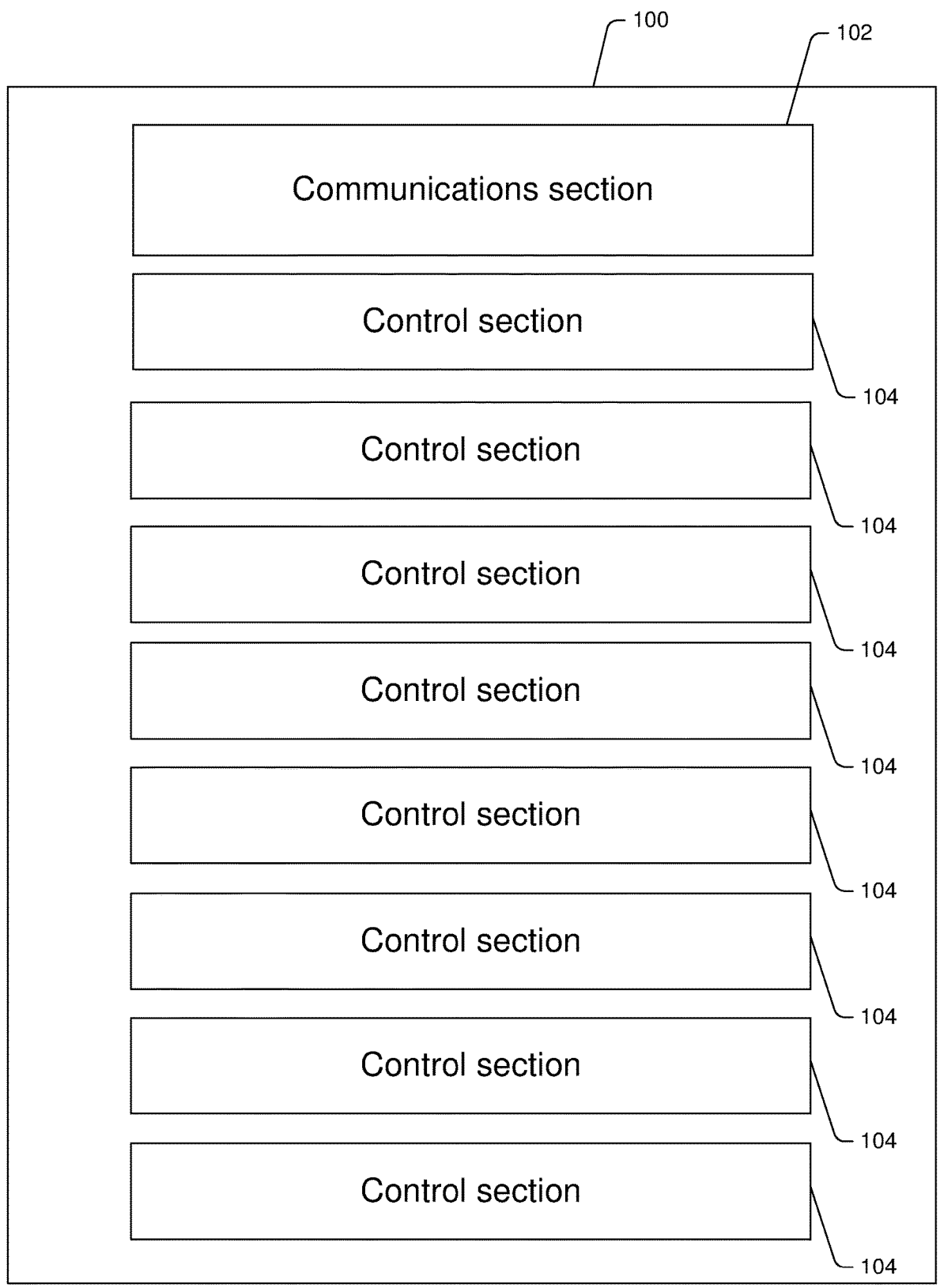
FIG. 1B is a conceptual block representation of a controller according to another embodiment of the invention.

In an embodiment shown in FIG. 1B, controller 100 includes a plurality of control sections 104, the illustrated embodiment specifically including eight control sections (each identical to control section 104 and, as such, the same reference number is used). As each control section will only has one I/O layer, such embodiments are used when more I/O layers are needed, in this case the eight controller modules (and therefore eight I/O layers). The number of I/O layers in the control section will be chosen based on the number of additional inputs and outputs are required for the desired measuring, metering and monitoring functionality of controller 100.

Figure 4:
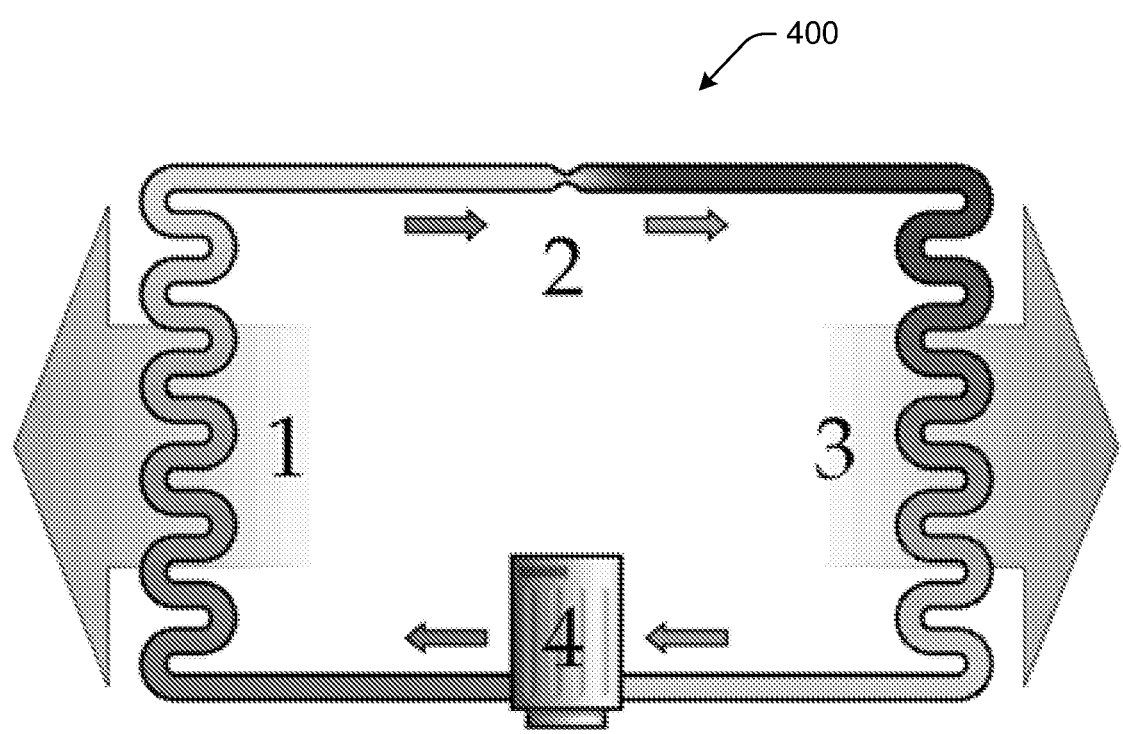
FIG. 4 is a known air conditioning or refrigeration circuit.

HVACR system 101 is essentially the same as the known system illustrated in FIG. 4 and denoted by reference 400, and includes chilled water supplied from a chiller or chillers with system 101 having water circulation through a cooling coil and a variable speed fan for directing air across the cooling coil. In embodiments, HVACR system 101 includes up to six cooling units. In other embodiments, HVACR system includes one or more single speed fans. In yet other embodiments, other types of cooling or refrigeration systems are utilised and equally compatible with controller 100.

Extra Sensors 207 interface to control section 104 via one or more of: Modbus, DRED, digital inputs/outputs and analogue inputs/outputs. Sensors 207 include but are not limited to:

Temperature sensors for measuring the temperature of the system and the temperature of the space to be cooled, amongst others.

Pressure sensors for measuring the pressure drop across a filter of the HVACR system and/or the cooling coil.

Flow sensors for measuring a water flow rate through the chilled water system via variable speed control of chilled water and condenser water pump(s).

Humidity sensors for measuring the humidity of the system and the humidity of the space to be cooled, amongst others.

Volatile organic compound (VOC) sensors for measuring indoor air quality.

As noted above, current sensors can take the form of current transformers (CTs). Regarding the use of CTs, these perform different functions within the controller, including:

Measuring current of individual components within a single HVACR System such as an air conditioning system, such components including a supply air fan and any one of the compressors;

Measuring total air conditioning current but tabling the values relative to any one of: the supply air fan; and any one of the compressors;

The controller identifies the individual values, which in turn provides positive feedback in the form of actual running performance of the individual components compared to the output functionality of the controller. If current ranges go outside the selected ranges being monitored by the controller an alarm will be raised via communications section 102 which will alert by text, email, dashboard screen or local alarm.

The current to a Variable Refrigerant Flow (VRF) or inverter is measured and also used to determine the most effective optimisation level relative to the refrigeration load of the air conditioning unit. This directly relates to current consumption when interfacing to an air conditioning unit with a Demand Response Enable Device (DRED).

The remote controller terminals are able to instruct control section 104 to enable the selective controlling. Web application 103 is accessible, in different embodiments, from a programmable computer, a portable computer, a dedicated terminal able to display and manipulate data, and a suitably programmed mobile phone or similar device. Moreover, in embodiments, the remote controller terminal is at a location remote from control section 104 and is in communication with it by known communication means.

In one embodiment, the remote controller terminal itself learns how to improve the energy efficacy of system 101 from information obtained via communication section 102. This information is received from other optimisation modules 100 operating within the same system 101 and sending information back to the remote controller terminal to make adjustments for the area monitored by those optimisation modules.

Control section 104 receives instructions from web application 103 to selectively control the functioning of a number of components of HVACR system 101. For example, for the variable fan speed chilled water system, control section 104 controls the circulation flow rate of water circulation through the cooling coil, and also controls the air flow rate (fan speed) of the fan across the cooling coil via variable speed control of fan motors.

Generally speaking, the sum of the sensors is assessed by system control section 104 to make comfort or optimization adjustments and/or monitor data from the sensors for analysis purposes.

The sensors and controlling of components of HVACR system 101 are all based on the set point or the operation of an un-loader valve of HVACR system 101. The activation and deactivation of the compressor will maximize energy efficacy of the system while maintaining the preselected average temperature in the space.

A single unit of controller 100 is connectable to another unit via BUSNET or wireless communication. In other embodiments, there are multiple units of controller 100 utilized in the one system.

Control section 104 includes several protocols that achieve the desired interface, and they include: RS232/485, Modbus and Building Automation and Control Network (BACnet), amongst others, all of which are international interfaces.

Although it is implicit, it is mentioned for completeness that communications section 102 connects to control section 104 internally within controller 100. In other embodiments, the Health and Usage Monitoring (HUM) can be carried out using a completely independent operation on an ACR asset and controller 100 can be used to interface to a unit next to it and carry out that function at the same time.

Controller 100 is a significant improvement over known systems, that would require a completely different piece of hardware with a far greater footprint to be able to perform additional functions. The footprint of controller 100 is approximately 120 mm×120 mm, a maximized sized unit with other industry standard single function systems having a much larger footprint. In another embodiment, the footprint of controller 100 is approximately 100 mm×100 mm. In yet another embodiment, footprint of controller 100 is approximately 80 mm×80 mm.

Control section 104 operates in conjunction with control software 204 that calculates optimal performance based on inputs and directs the HVACR device (via control section 104) to operate in a specific manner. Furthermore, control software 204 is configurable to optimally operate different types of HVACR system.

As noted above, a single controller generally operates a single air conditioning unit. However, up to 250 controllers can be linked together forming a BUSLINK communication via the LAN communications ports on controller 100 and in this case, all of the linked controllers can be individually accessed through the LAN Busway.

Existing optimisation systems generally only assess one or two parameters of a system and have no awareness of the total system operation. As noted above, the optimisation of the different ACR assets such as 1, 2, 4, or 8 compressor systems and chiller systems traditionally required very different optimisers. However, controller 100 is able to optimise all of these systems. Controller 100 can also be relocated from a system of one technology to a system of any other of the technologies, with the associated software program being selected to operate on the technology.

Controller 100 allows for:
The continued optimisation of compressors at asset level (as in at the level of each individual unit).
Combination of a controller with built-in optimisation.
One device to interface to all known systems including:
Single Compressor.
Multiple compressors or stages up to 8.
Chillers for air conditioning systems.
Chillers for refrigeration systems.
Inverter systems.
Variable refrigerant flow (VRF) systems.

Furthermore, controller 100 may optimise any of the following specific compressor systems:
Simple fixed speed compressor with a refrigeration capacity from 2 kWr to 30 kWr:
This interface optimises the compressor relative to the cycling of the compressor and or the operating space temperature and is a hard-wire interface.
Variable speed Compressors for inverter and VRF systems with a specific DRED or Modbus interface:
This interface optimises the compressor relative to the motor current being consumed and or the space temperature. If it is a DRED interface it is a hard-wire interface. If there is a Modbus connection it is a high level interface and the change parameters are set up within controller 100 which provides instruction via the Modbus to initiate optimisation within the system.
Single speed reciprocating compressor with up to 4 unloading stages:
This system optimises relative to the unloading of the compressor and either the space temperature or if it is a chilled water system it operates relative to the chilled leaving chilled water temperature. This is a hard-wired interface.
Systems with multiple compressors from 2 to 8 compressors:
These systems are optimised relative to the cycling of the compressors and the space temperatures.
If they are larger refrigeration systems, which are controlled relative to suction pressure then an additional refrigerant pressure transducer is installed for the system to optimise relative to the suction pressure.
Screw compressor systems generally have a proprietary control system which has either a low level input point (0 to 10 VDC or 4 to 20 mA) which are set up within controller 100 to provide variants of this signal to integrate with the system to provide optimisation of functionality to the system.
Screw chillers can also be interfaced via their unloading solenoid valves, which can be up to four stages. Depending on the control platform being temperature or suction pressure, a staged solution is used.
Centrifugal compressor systems are as above, except for unloading valves.
If the screw and centrifugal compressor systems have an existing higher level control from either a supervisory control and data acquisition (SCADA), programmable logic control (PLC) system or a BMS which are already providing set point adjustment, this existing system is interfaced with controller 100 either via a low level interface from a 0 to 10 VDC or 4 to 20 mA output from controller 100 or via Modbus or BACnet interface and the optimisation to the compressor is affected by providing this additional information via the interface.

In addition to the basic optimisation of compressor operation in every type of air conditioning and refrigeration system controller 100 can also provide:
System Control.
Asset monitoring and reporting possibilities for package air conditioning units and air handling units including for:
Space temperature.
Temperature differential across the coil.
Pressure differential across the coil.
Pressure differential across the filter.
Air flow at the coil face.
Duct air pressure.
Variable speed drives (VSD) control.
Fan amps.
Compressor amps.

Whole of single asset energy consumption.
Live monitoring of each of the above parameters.
Fault reporting and alarming.
Asset monitoring and reporting possibilities for chillers including:
Leaving and entering water temperature.
Biofilm colonization of the cooling tower and water circuit.
Chiller flow rates.
Chiller pressures.
Compressor amplifiers.
Whole of chiller energy consumption.
Live monitoring of each of the above parameters.
Fault reporting and alarming.

In addition to the basic optimization, controller 100 reports on all of the aforementioned systems for:
Continued operation or compressor fault via a current transformer.
Operating temperatures.
Coil differential temperature.
Pressure drop across the coil.
Air flow at the coil face.
Current consumed by the fan.
Over temperature.
Under temperature.
Compressor failure.
Fan failure.
Other parameters as required by a specific process or client requirements.
Indoor air quality.
Full Power metering and monitoring with revenue grade meters measuring:
kW
kWh
kVa
kVar
Power Factor
Amps (3 phase or single phase)
Line Voltage Controller 100 can also integrate to BMS's or SCADA systems to become an integrated part of that total operating platform.

In some embodiments, the power monitoring is relative to the unit being controlled and/or optimised by controller 100. In other embodiments, the power monitoring is of other systems or the entire site at the same time.

In some embodiments, controller 100 is a non-communicating, non-networked device that is initially programmed and left isolated to carry out the programmed functionality. In the more preferred embodiments, controller 100 is a fully networked and interoperable control and compressor optimisation device. In other embodiments, varying levels of communication and network connectivity are utilized depending on the particular circumstances and requirements of a setup.

Communications section 102 is accessed by a web interface that communicates with the inbuilt modem.

Control software 204 includes programs that take inputs from the digital inputs (for example thermostat outputs) and analogue inputs (for example thermistors and current transformers) of control section 104. The programs shall implement algorithms to optimise and/or control HVACR system 101. Digital outputs (for example compressor on/off signal, heating on/off signal) as well as analogue outputs (for example chiller set point) are set by the program.

The programs can also be bypassed so HVACR system 101 can run as usual.

Notably, the programs are adjustable, with the adjustable elements including all temperatures, on periods and off periods associated with so HVACR system 101. Programs with control systems shall implement control loops based on temperature rather than a thermostat signal.

In some embodiments, parameter data is logged to internal storage at a rate of once per minute, with all log entries shall be time-stamped. The logging file type shall be flexible to allow different parameters to be logged in different types of systems and the log files will be kept on communications section 102 for a minimum of one year. In other embodiments, the data will be retained for other than a minimum of one year. Where appropriate, the minimum and maximum value over the logging internal will be stored for each parameter.

The following data shall be logged (if available in that system):
Date/Time in the form [dd/mm/yyyy hh:mm:ss]
Temperature [degrees C./F]
On/Off time for each compressor [hours]
Requested on time for each compressor (accumulation of thermostat signal) [hours]
Time in bypass mode [hours]
Time in save mode [hours]
Time in temperature override mode [hours]
System Current [Amps]
Compressor Current [Amps]
Fan Current [Amps]
Pressure [PSI/Bar/kPa]
Water Temperature [degrees C./F]
Set point(s) [degrees C./F for temperature, PSI/Bar/kPa for pressure]
Temperature differential across compressor coil [degrees C./F]
Pressure differential across evaporator coil [PSI/Bar/kPa]
Pressure differential across the filter [PSI/Bar/kPa]
Air flow at the evaporator coil face [m/s]
Duct air pressure [PSI/Bar/kPa]
Chiller pressure [PSI/Bar/kPa]
Variable Speed Drive (VSD) control setting
Data from third part Power Monitoring System, including:
Voltage [V]
Current [A]
Power [kW]
Power Usage [kWh]
Power Factor [%]
List of system alerts Control software 204 has drivers for the following hardware:
Current Transformers (CT)
Temperature Sensor (PT100)
Digital Inputs
Digital Outputs
Analogue Inputs
Analogue Outputs
DRED Interface
BACnet
Modbus Any analogue input or output (including CTs) have the option of linear calibration to take into account any differences in analogue to digital converter (ADC) or digital to analogue converter (DAC) performance or in setup of HVACR system 101.

Controller 100 interfaces to a third party power monitoring system via ModBus. The parameters shall be logged as described above.

Programming is protected to minimise tampering. This includes parameter range checking on web controlled parameters, password protection on all forms of access, firewall on direct access to the hardware of communication section 102 and control section 104.

System 200 supports programs for the following optimisation only system types:
Fixed Speed Single Compressor
Single Speed Inverter Should be Variable Speed Inverter
Variable Refrigerant Volume (VRV)
Tri Stage
Fixed Speed Dual Compressor
Fixed Speed 4 Compressor
Fixed Speed 8 Compressor System 200 supports programs for the following controller with optimisation system types:
Fixed Speed Single Compressor
Fixed Speed Dual Compressor
Fixed Speed 4 Compressor System 200 supports chiller control and allows the addition of other system types with little or no modifications.

System 200 keeps track of date and time and therefore is able to turn the HVACR system 101 on and off at particular times on a weekly basis.

As noted above and in FIG. 2, web application 203 shall support different user types—an end user and a technician.

End User Interface 201 allows control of the temperature set point within a very narrow range and shows the following information on a dashboard:
Temperature
Power
Current
Current Compressor Status Technician Interface 202 includes all the features of End User Interface 201 and in addition includes:
Updating all program parameters
Reprogramming software
Ability to download all log files
Ability to set/read any input or output (other than outputs currently being controlled by the software algorithm)

System 200 is also capable of generating SMS and e-mail alert, the types of alerts being configurable from web interface 203. Alert types include:
System reboot—Including reboot reason if known
No SD Card
SD Card close to full
SD Card full
Digital input reading does not match digital output setting
Any measured analogue input outside of expected range, including:
  Current
  Temperature
  Pressure
  Temperature differential
Driver set/read error
Loss of communications to Modbus devices
Loss of communications to control section 104
Total compressor on-time reaching a limit
Total number of compressor on/off cycles reaching a limit
Tamper alert (any unauthorised log on attempts)

In embodiments, system 200 will also be capable of live monitoring of any inputs and outputs and has a low level control mode for adjusting any outputs.

Figure 3:
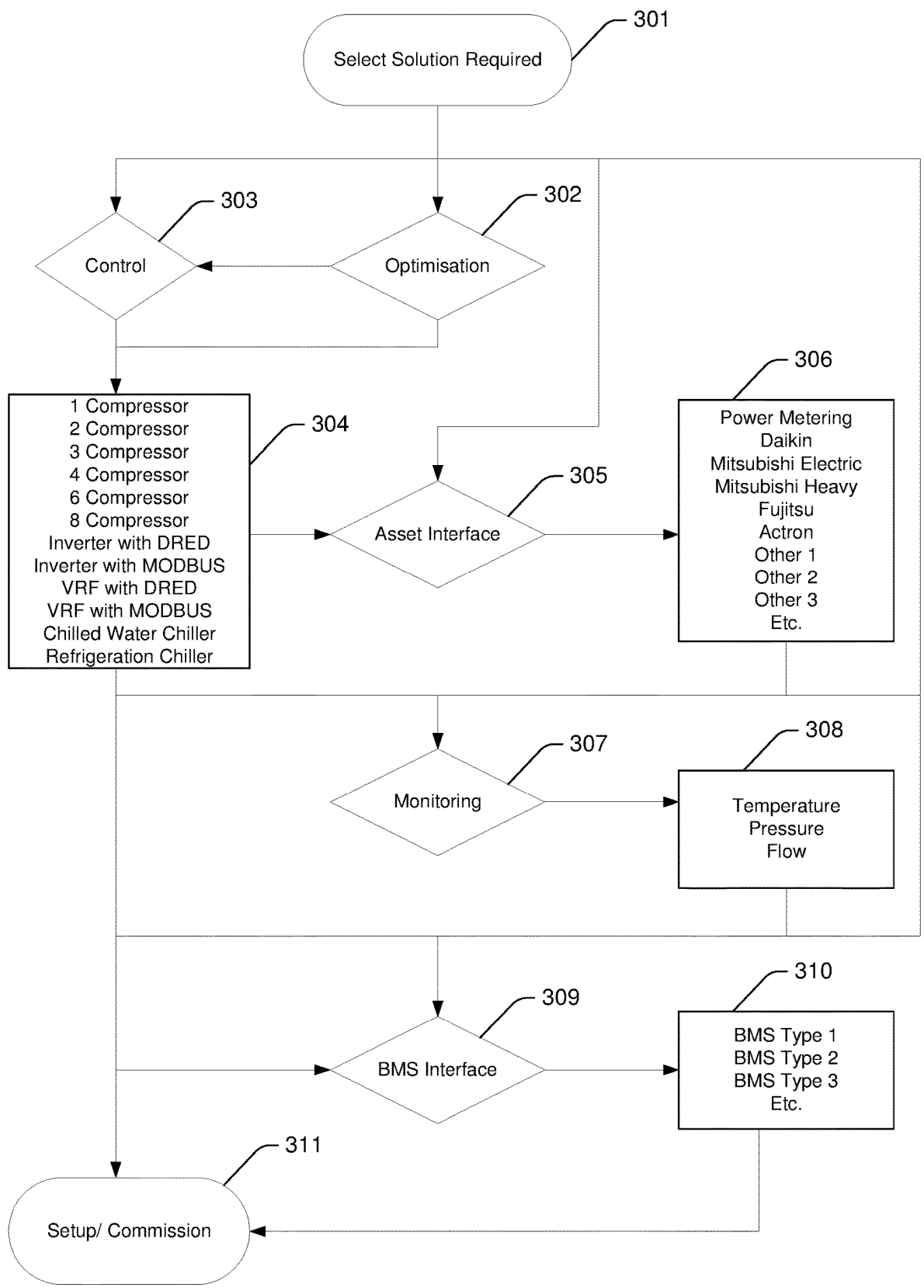
FIG. 3 is a flow chart illustrating the operation of the controller and system of FIGS. 1A and 2 respectively.

Referring to FIG. 3, the process for setting up system 200 is done through web application 203. Step 301 is the selection of a particular solution, a solution being, for example, to control the functioning of a number of air-conditioning units for a commercial building. This triggers control software 204 to come up with an initial optimised operation algorithm at step 302 which is inputted into controller 100 at step 303. This optimized operation is based on maintaining a certain set point parameter at a given level (although the set point may change), and in preferred embodiments this set point parameter is the "leaving/exit water temperature point" of an HVACR system. Therefore, in order to maintain the exit water temperature at a pre-defined temperature, controller 100 will proceed to control specific types of HVACR system assets, some of which are listed within the box labeled with reference numeral 304. This controlling involves the regulating the performance of a number of components of the HVACR system, for example, turning a single speed fan on or off, slowing down or speeding up a variable speed fan, slowing down or speeding up water flow through a chilled water system, amongst others. The asset interface, at step 305, receives input from both the control software 204 and the individual asset and provides this information to the HVACR system, some of which are listed within the box labeled with reference numeral 306. The output of both the individual asset and the HVACR system are monitored by monitoring system 206 at step 307, with the monitoring parameters including temperature, pressure and flow, which are listed within the box labeled with reference numeral 308. Finally, at step 309 the BMS interface receives inputs from the individual asset, the HVACR system and the monitoring system 206, the box labeled with reference numeral 310 showing some generic different types of BMS's. The setup of system 200 is them completed (denoted by step 311) and regular functioning of the controller and system will commence.

As noted above, the functioning of controller 100 works off 'changing set points'. That is, a certain set point (for example, a certain exit water temperature point) will be initially set to achieve a desired room temperature. Based on data received from sensors 207 that are monitoring certain aspects of HVACR system 101, amongst others, the data will be fed back into control software 204 such that the operation algorithm will be adjusted which in turn changes the set point.

Based on the above adjustment of operation algorithm, controller 100 and therefore system 200 is an automated self-improving intuitive system that essentially 'learns' to function more efficiently through feedback.

In other embodiments, the set point parameter is other than exit water temperature. In an embodiment where the HVACR system is a refrigeration system, the set point parameter is the refrigeration system suction pressure or temperature. In cases where the set point parameter is suction pressure the associated measurement parameter such as PSI, Bar or Kpa can be selected to suit.

In other embodiments, controller 100 uses set point parameters other than those mentioned above. In yet other embodiments, controller 100 uses multiple set point parameters.

The functioning of controller 100 is advantageous over other known devices which use a relatively simple controller functioning on a 'fixed timing basis' which involves simply turning fixed speed HVAC systems on/off and/or slowing down the speed of variable speed HVAC systems.

Another example for the advantageous functioning of controller 100, is a situation where dust builds up on the filter of an HVACR system. Such a build up causes the airflow to be inhibited and the air flow pressure to drop which, in turn, causes the HVACR system to work harder to provide the requisite cooling. Controller 100 is able to identify the drop in pressure and can infer that this is caused by a dust filter. Controller 100 can then provide feedback recommending the filter be cleaned or replaced.

As mentioned earlier, biofilms present on the heat exchange coils cause significant challenges when looking to optimize the energy efficiency of cooling and refrigeration systems. It has been noted by the present applicant that even greater savings can be attained by using controller 100 in conjunction with a specific "coil treatment" of the evaporator coil. In addition, biofilms present in the cooling tower and water circuit negatively impact heat exchange efficiency and cause significant health challenges associated with *Legionella* bacteria.

Biofilms are notoriously difficult to clean from surfaces because attachment is tenacious by virtue of exuded proteins and mucopolysaccharides from the cells to the substrate and polysaccharides and other carbohydrates creating adhesion between the cells. Further, biofilms exhibit a surface "slime" containing amongst a variety of other biological molecules, dead cells, with this layer protecting the biofilm from biocides and other mechanisms which would otherwise facilitate its removal.

Traditionally biofilms have been removed by drying affected surfaces and then using force exerted, by ultra high pressure water blasting or by long exposure to streams of highly alkaline detergents.

None of these traditional techniques can be used on heat exchange cooling coils because they are typically constructed from closely packed (a gap of 2-3 mm is common), unanodised aluminium with thin, flexible cooling fins attached to copper tubing through which refrigerant travels. Even if drying was an option, which it is usually not, abrasion between the fins cannot be used as high pressure water blasting destroys the edges of the soft aluminium fins and any alkali immediately begins to cause severe corrosion to unanodised aluminium.

The "coil treatment" for cooling coils employed in the present case is a two-step process involving firstly a multi enzymatic cleaning of the coils and secondly the application of a biostatic polymeric film.

Every enzyme can typically digest only one class of biological molecule. It has been demonstrated in a wide variety of field trials that a combination of a proteolytic enzyme or protease (digests proteins), an amylase (digests polysaccharides), a cellulase (digests cellulose and associated carbohydrates) and a lipases (digests triglycerides) can successfully digest biofilms growing on heat exchange cooling coils across a wide variety of geographies and environments. Furthermore these enzyme formulations exhibit a near-neutral pH and therefore have no corrosive implications towards the cooling coils. Typically these formulations present as aqueous concentrates which are diluted with warm water at the point of use, sprayed onto all effective areas of the cooling coils, allowed to stand for at least 20 to 30 minutes and then rinsed off with low pressure water. This process has been found to efficiently eliminate biofilm.

Suitable cleaning regimes are detailed in previous published patent applications of Novapharm Research (Australia) Pty Ltd, such as PCT publication number WO/2009/135259 (entitled "Instrument Cleaner", PCT/AU2009/000564) and PCT publication number WO/2008/009053 (entitled "Low Foaming Cleaner", PCT/AU2007/000999).

In one embodiment, the cleaning regime involves the use of a composition comprising a protease and a biostatically effective phenoxyalcohol. In embodiments, the composition advantageously includes one or more hydrolases and optionally boron or a boron compound as an activity protector.

In another embodiment, the cleaning regime involves the use of a surfactant-free composition which contains a protease and optionally in addition one or more hydrolase enzymes including but not limited to lipases, cellulases and amylases. The surfactant-free composition also includes a water soluble glycol ether solvent, at least one anionic hydrotrope (typically an alkali metal alkylarylsulphonates such as sodium xylene sulfonate or cumene sulfonate).

In yet another embodiment, the cleaning regime involves the use of a liquid composition comprising: one or more enzymes (for instance a protease and an amylase), a biocidal quaternary ammonium biocide, and an anionic hydrotrope. The liquid compositions may include boron or a boron compound as activity protector and/or a polyol having from 2 to 6 hydroxyl groups.

All the cleaning regimes above can be customised to the specifics of the biofilm and the enzymic components mentioned can be expanded to a full multi-enzyme range (protease, amylase, cellulase and lipase) if necessary.

Biofilm quickly begins to regrow on cooling coils upon recommencement of the cooling function. Therefore, to preserve optimal heat exchange properties a treatment for these effective surfaces is required.

The second part of the "coil treatment" process involves the application to the newly cleaned surface of a film comprising one or more commonly used biocides complexed (not reacted) with hydrophilic but water insoluble polymers. In both cases the polymer/biocide complex can be dissolved in ethanol and is sprayed onto the coil surfaces after the biofilm has been digested and rinsed away. Typically, the treatments last for between 12 months and 36 months whereafter the surfaces must be again cleaned and treated. There biocides and polymers are as disclosed in Novapharm Research (Australia) Pty Ltd's previous published patent applications, such as PCT publication number WO/2004/103071 (entitled "Biofilm Growth Prevention", PCT/AU2004/000650) and PCT publication number WO/2006/081617 (entitled "Biostatic Polymer", PCT/AU2006/000130), the disclosures of which are incorporated herein by reference.

One treatment involves the application of a solution of a phenolic biocide and polyvinylpyrrolidone or polyvinylpyrrolidone polymers or copolymers, such as acrylic copolymer based compositions, methacrylic copolymer based compositions, vinyl copolymer based compositions, epoxy resins, epoxy esters, and mixtures thereof.

Specifically preferred is a polyvinylpyrrolidone/polyvinylacetate copolymer complexed with triclosan.

Another treatment involves the application of a solution of a quaternary ammonium biocide and a compatible polymer, such as polyvinyl alcohol, or a half ester of maleic anhydride/alkylvinylether copolymer complexed with a quaternary ammonium biocide.

In fact, surprisingly to the inventor, trials have shown that use of the controllers described herein along with specific treatments as described above of the evaporator coil will increase the cost savings by a total that is greater than the sum of the parts. The below table shows the results of a number of trials that each took place over the period of one week:

| | Trial 1<br>AC Controls Only | | Trial 2<br>Optimiser Only | | Trial 3<br>Coil Treatment Only | | Trial 4<br>Optimiser & Coil Treatment | |
|---|---|---|---|---|---|---|---|---|
| kWh | 431.2 | kWh | 389.0 | kWh | 401.65 | kWh | 333.6 | |
| Relative Humidity | 76% | Relative Humidity | 94% | Relative Humidity | 68% | Relative Humidity | 75% | |
| Min Temp | 22.9 C. | Min Temp | 24.1 | Min Temp | 24.0 | Min Temp | 25 | |
| Max Temp | 30.1 C. | Max Temp | 30.0 | Max Temp | 30.3 | Max Temp | 30.4 | |
| | | Optimisation Saving | 9.80% | Treatment Saving | 6.90% | Combined Saving | 22.60% | |

As shown in the above table, the controller in alone (Optimiser Only') provides significant energy savings over the normal functioning CAC Controls Only'). Moreover, the 'coil treatment' in alone (Coil Treatment Only') provides significant energy savings over the normal functioning. However, as noted above, the combination of the two technologies provides an unexpected synergy, providing an energy saving that is a greater saving than the sum of the parts.

Looking at the 'AC Controls Only' functioning, when build-up starts to form on the coils due to overuse of the HVACR system, this reduces the output of the HVAC system and therefore causes it to work harder (that is, consume more power) to achieve a certain room temperature. This results in much greater variance in room temperature due to the system working harder and turning on/off more often in order to attempt to achieve and maintain the desired temperature. Such behaviour is a result of the relatively simplistic functioning capabilities of known devices. However, controller 100 for the 'Optimiser Only' functioning receives more feedback information and is able to do more with this information in order to change its behaviour to more efficiently achieve the desired temperature. This results in much less drastic temperature changes and much less strain on the HVAC system.

Each software program for optimisation of HVACR system 101 follows a set of rules. If a certain condition is detected, then the program will act accordingly. The following are examples only and it noted that all numerical values will be configurable, particularly to adjust timing parameters. Some program examples are set out below.

Example A.1: Single Compressor Fixed Speed System—Optimisation Only

The Inputs/Outputs used are: Temperature reference, One Digital Input (Thermostat) and One Digital Output (Compressor).

All operation is based on detected the period of time the thermostat is requesting the compressor to be on and off.

The rules for this example are as follows:
A.1.2.1 If short cycling is detected a 7 minute off period will be applied to the compressor.
A.1.2.2 If the on time is between 10 and 20 minutes a 6 minute off period will be applied to the compressor.
A.1.2.3 If the on time is between 20 and 30 minutes then two 6 minute off periods must be applied to the compressor within a 30 minute period. There must be at least 10 minutes between off cycles. Note: Times to be adjusted as 6+10+6+10=32.
A.1.2.4 If the on time is greater than 30 minutes then a 7 minute off period will be applied to the compressor.
A.1.2.5 If an override temperature is reached (greater than a maximum when cooling or less than a minimum when heating) then the system will go into a bypass mode where the thermostat directly controls the compressor. This mode continues until the temperature is back inside the override temperature by a margin of 1° C.
A.1.2.6 If there has been no thermostat input for more than an hour the software will determine that the system has been switched off (i.e., overnight). This mode will override rule 5.
  A.1.2.6.1 If there is an on time of more than 21 minutes after this a 6 minute off period will be applied.
  A.1.2.6.2 If there is a further on time of 21 minutes after the initial 6 minute off period then a 7 minute off period will be applied.
  A.1.2.6.3 A cycle of 21 minutes on and 7 minutes off will be applied until the thermostat signal turns off.
  A.1.2.6.4 After this point the cycle will revert to rules 1 through 4.
A.1.2.7 Short Cycling: This is a condition where the compressor is turning off and on at its minimum period. The system will define short cycling as when the following sequence is detected:
  4 minutes on;
  4 minutes off;
  4 minutes on; and
  4 minutes off.

Example A.2: Two Compressor Fixed Speed System—Optimisation Only

The Inputs/Outputs used are: One Temperature Reference, Two Digital Inputs (Thermostat Stage 1, Thermostat Stage 2) and Two Digital Outputs (Compressor 1, Compressor 2), Three Analogue Inputs, and CT Input per compressor.

The rules for this example are as follows:
A.2.2.1 Under low load conditions (where the thermostat only has one output on) this system will follow the rules of the one compressor fixed speed system.
A.2.2.2 In low load conditions only compressor 1 will be used.
A.2.2.3 When the second thermostat output is on the second compressor will run as per the rules of the one compressor fixed speed system and the first compressor will stay on.

Example A.3: Four Compressor Fixed Speed System—Optimisation Only

The Inputs/Outputs used are: One Temperature Reference, Four Digital Inputs (Thermostat Stage 1, Thermostat Stage 2, Thermostat Stage 3, Thermostat Stage 4), Four Digital Outputs (Compressor 1, Compressor 2, Compressor 3, Compressor 4), One Analogue Input, CT Input per compressor, and One Analogue Output.

The rules for this example are as follows:
A.3.2.1 Under low load conditions (where the thermostat only has one output on) this system will follow the rules of the one compressor fixed speed system.

A.3.2.2 In low load conditions only compressor 1 will be used.
A.3.2.3 When the second thermostat output is on the second compressor will run as per the rules of the one compressor fixed speed system and the first compressor will stay on.
A.3.2.4 When the third thermostat output is on the third compressor will run as per the rules of the one compressor fixed speed system and the first and second compressors will stay on.
A.3.2.5 When the fourth thermostat output is on the fourth compressor will run as per the rules of the one compressor fixed speed system and the first, second and third compressors will stay on.

Example A.4: Chiller Optimisation

The Inputs/Outputs used are: One Water Temperature Reference, Multiple Digital Inputs (depends on particular chiller), Multiple Digital Outputs (depends on particular chiller), CT Input, and One Analogue Output for water set point.
The rules for this example are as follows:
A.4.2.1 Optimisation involves changing the set point for the chiller. The set point will be increased by a known factor for a period between 5-11 minutes once per half hour.
A.4.2.2 The time that the set point is increased depends on how far above the set point the water temperature reached during the last half an hour.
A.4.2.3 If the water temperature goes too high, optimisation will be bypassed.

Example A.5: Heat Pump Optimisation

The Inputs/Outputs used are: One Temperature Reference, Four Digital Inputs (Thermostat Stage 1, Thermostat Stage 2, Thermostat Stage 3, Thermostat Stage 4), Four Digital Outputs (Compressor 1, Compressor 2, Compressor 3, Compressor 4), One Analogue Input and CT Input per compressor.
The rules for this example are as follows:
A.5.2.1 A standard OFF time will be applied to each compressor four times per hour.
A.5.2.2 The OFF time will decrease if the temperature drops below the set point.
A.5.2.3 The OFF time will increase if the temperature rises above the set point.
A.5.2.4 The compressor off cycles will be rotated amongst the compressors to balance compressor operating time.

Example A.6: Tri Stage Optimisation

The Inputs/Outputs used are: One Temperature Reference, Three Digital Inputs, and Three Digital Outputs.
The rules for this example are as follows:
A.6.2.1 When inputs one and three are on, output 1 will be turned on until input three is off;
A.6.2.2 When inputs two and three are on, output 2 will be turned on until input three is off; and
A.6.2.3 When all inputs are on, output 3 will be turned on until input three is off.

Example A.7: Inverter Optimisation

The Inputs/Outputs used are: One Temperature Reference, One CT Input, One Digital Input, and Three Digital Outputs.

The rules for this example are as follows:
A.7.2.1 When current consumption is between 80-100% after 20 minutes output three will be turned on for 7 minutes;
A.7.2.2 When current consumption is between 50-79% after 20 minutes output two will be turned on for 8 minutes; and
A.7.2.3 When current consumption is between 10-49% after 20 minutes output one will be turned on for 8 minutes.

CONCLUSIONS

Controller 100 is advantageous over the prior art for a number of reasons including:
Allows modification and recalibration of the controller to suit any type of HVACR system. As noted above, this kind of modification would normally require very specific third party systems and solutions and this would be done either at the unit itself, via a 3G modem link or via a third party interface.
The design of the HVACR system is not changed at all. Controller 100 only alter the functioning of the system in order to maximize energy savings.
Can relocate the unit from and to any other asset and set it up to become that unit.
Automated, self-improving, intuitive system that essentially 'learns' to function to save power.
The unit reduces the power required to run an HVACR system, resulting in significant energy savings.
When used in conjunction with the two step 'coil treatments' described herein, the resulting energy savings are even greater than the sum of the savings for the unit and 'coil treatments' working independently.
The relatively miniature size of the unit and in particular the relatively small footprint.
It has been designed to operate in conjunction with specific non-electronic solutions.

There are many systems which can be used to carry out multiple functions in the control, monitoring, management and reporting areas but there is no single device capable of providing this level of operation of assets and other intelligent systems as does the devices and system described herein.

Apart from its size its particular configurability to make any of our solutions work within a single unit and the ability of controller 100 to operate up to 250 slave units all carrying out different functions and operations on all of the different assets and its ability to also interface at high level to any third party system all from the one unit makes it very unique.

Controller 100 provides complete flexibility within a system to be many systems and solutions within the one system.

The existing optimiser systems cannot assess the functionality of other essential parts of an air conditioning or refrigeration system such as the evaporator or cooling/heating coils and their efficiency, which in turn has an effect on the ability of the optimiser to perform. As mentioned previously, if a third party needed to do this, a separate controller would need to be installed to carry out this functionality.

The optimisation of the different assets such as 1, 2, 4, and 8 compressor systems and chiller systems would otherwise require very different optimisers. Controller 100 can optimise all of these solutions with the one system. It can also be relocated from one technology to any of the other technologies and the associated program is selected to operate on the technology.

The physical parameters required for controller 100 are as follows:
- Expandable beyond the current generation of technology.
- Modular in design and expandability.
- Accessible in any installation around the world down to asset level if required.
- Software and functionality changes via the IoT.
- Small footprint (miniaturisation).
- Will work in conjunction with other products (such as chemical treatments) to provide even further efficiencies.

Interpretation

Throughout this specification, use of the term "element" is intended to mean either a single unitary component or a collection of components that combine to perform a specific function or purpose.

Unless specifically stated otherwise, as apparent from the following discussions, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "controller" or "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one of more of the methods described herein. Note that when the method includes several elements, e.g., several steps, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Reference throughout this specification to "one embodiment", "some embodiments" or "an embodiment" means that a particular feature, structure or characteristic described in connection with the embodiment is included in at least one embodiment of the present disclosure. Thus, appearances of the phrases "in one embodiment", "in some embodiments" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

It should be appreciated that in the above description of exemplary embodiments of the disclosure, various features of the disclosure are sometimes grouped together in a single embodiment, Fig., or description thereof for the purpose of streamlining the disclosure and aiding in the understanding of one or more of the various inventive aspects. This method of disclosure, however, is not to be interpreted as reflecting an intention that the claims require more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical, electrical or optical contact, or that two or more elements are not in direct contact with each other but yet still co-operate or interact with each other.

Thus, while there has been described what are believed to be the preferred embodiments of the disclosure, those skilled in the art will recognize that other and further modifications may be made thereto without departing from the spirit of the disclosure, and it is intended to claim all such changes and modifications as fall within the scope of the disclosure. For example, any formulas given above are merely representative of procedures that may be used. Functionality may be added or deleted from the block diagrams and operations may be interchanged among functional blocks. Steps may be added or deleted to methods described within the scope of the present disclosure.

I claim:

1. A method for reducing the energy usage of a heating, ventilation, air conditioning and refrigeration (HVACR) system having an optimizing controller capable of operating the HVACR system and at least one evaporator coil, the optimizing controller including:
    a communications section for communicating with at least one remote controller terminal; and
    a control section operatively associated with the HVACR system for selectively activating or deactivating the at least one evaporator coil based on one or more settings received from the at least one remote controller terminal via the communications section;
    wherein the method comprises providing a coil treatment to the at least one evaporator coil, such that the use of the controller in conjunction with the coil treatment reduces the energy usage of the HVACR system by over 15%;
    wherein the coil treatment comprises:
        i) a first enzymic cleaning step comprising contacting the coil with an enzymic cleaning solution to provide a cleaned coil; and
        ii) a second step comprising coating the cleaned coil with a biostatic polymeric coating;
    wherein the enzymic cleaning solution comprises one or more of a protease, amylase, cellulase or lipase.

2. A method according to claim 1 wherein the enzymic cleaning solution comprises a protease and a biostatically effective phenoxyalcohol.

3. A method according to claim 1 wherein the enzymic cleaning solution comprises a protease, a water soluble glycol ether solvent and at least one anionic hydrotrope such as an alkali metal alkylarylsulfonate.

4. A method for reducing the energy usage of a heating, ventilation, air conditioning and refrigeration (HVACR) system having an optimizing controller capable of operating the HVACR system and at least one evaporator coil, the optimizing controller including:
    a communications section for communicating with at least one remote controller terminal; and
    a control section operatively associated with the HVACR system for selectively activating or deactivating the at least one evaporator coil based on one or more settings received from the at least one remote controller terminal via the communications section;
    wherein the method comprises providing a coil treatment to the at least one evaporator coil, such that the use of the controller in conjunction with the coil treatment reduces the energy usage of the HVACR system by over 15%;
    wherein the coil treatment comprises:
        i) a first enzymic cleaning step comprising contacting the coil with an enzymic cleaning solution to provide a cleaned coil; and
        ii) a second step comprising coating the cleaned coil with a biostatic polymeric coating;
    wherein the enzymic cleaning solution comprises one or more enzymes, a biocidal quaternary ammonium biocide, and an anionic hydrotrope.

5. A method according to claim 4 wherein the use of the controller in conjunction with the coil treatment reduces the energy usage of the HVACR system by over 18%.

6. A method according to claim 4 wherein the use of the controller in conjunction with the coil treatment reduces the energy usage of the HVACR system by over 20%.

7. A method according to claim 4 wherein the one or more enzymes comprises at least one of a protease or an amylase.

8. A method for reducing the energy usage of a heating, ventilation, air conditioning and refrigeration (HVACR) system having an optimizing controller capable of operating the HVACR system and at least one evaporator coil, the optimizing controller including:
    a communications section for communicating with at least one remote controller terminal; and
    a control section operatively associated with the HVACR system for selectively activating or deactivating the at least one evaporator coil based on one or more settings received from the at least one remote controller terminal via the communications section;
    wherein the method comprises providing a coil treatment to the at least one evaporator coil, such that the use of the controller in conjunction with the coil treatment reduces the energy usage of the HVACR system by over 15%;
    wherein the coil treatment comprises:
        i) a first enzymic cleaning step comprising contacting the coil with an enzymic cleaning solution to provide a cleaned coil; and
        ii) a second step comprising coating the cleaned coil with a biostatic polymeric coating;
    wherein the biostatic film comprises at least one of:
        phenolic biocide and polyvinylpyrrolidone or polyvinylpyrrolidone polymers or copolymers, such as acrylic copolymer based compositions, methacrylic copolymer based compositions, vinyl copolymer based compositions, epoxy resins, epoxy esters, and mixtures thereof;
        a polyvinylpyrrolidone/polyvinylacetate copolymer complexed with triclosan; or
        a quaternary ammonium biocide and a compatible polymer, such as polyvinyl alcohol, or a half ester of maleic anhydride/alkylvinylether copolymer complexed with a quaternary ammonium biocide.

9. A method according to claim 8 wherein the use of the controller in conjunction with the coil treatment reduces the energy usage of the HVACR system by over 18%.

10. A method according to claim 8 wherein the use of the controller in conjunction with the coil treatment reduces the energy usage of the HVACR system by over 20%.

\* \* \* \* \*